United States Patent
Merger et al.

[11] Patent Number: 5,003,089
[45] Date of Patent: Mar. 26, 1991

[54] PREPARATION OF CYCLIC 6-MEMBERED TO 8-MEMBERED VINYLENE-1,2-DIOXY COMPOUNDS

[75] Inventors: Franz Merger, Frankenthal; Juergen Frank, Schwetzingen; Wolfgang Hoelderich, Frankenthal; Toni Dockner, Meckenheim; Manfred Sauerwald, Meckenheim, all of Fed. Rep. of Germany

[73] Assignee: Basf Aktiengesellschaft, Ludwigshafen, Fed. Rep. of Germany

[21] Appl. No.: 379,412

[22] Filed: Jul. 13, 1989

[30] Foreign Application Priority Data

Aug. 3, 1988 [DE] Fed. Rep. of Germany ....... 3826303

[51] Int. Cl.$^5$ .................. C07D 321/08; C07D 319/12
[52] U.S. Cl. ................................. 549/333; 549/378; 549/377; 549/362; 549/350; 549/347; 549/13
[58] Field of Search ............... 549/378, 377, 362, 350, 549/347, 333, 13

[56] References Cited

U.S. PATENT DOCUMENTS 4,238,500 12/1980 Szent-Gyorgyi et al. .......... 549/364
4,386,018 5/1983 Merger et al. ...................... 568/862

OTHER PUBLICATIONS

J. heterocyclic Chem., 17, 831–832 (1980).
Chemical Abstracts, vol. 103, 104935v (1985).
J. Chem. Research (S), 273 (1977).
J. Org. Chem. 31, 389–391 (1966).

Primary Examiner—Nicky Chan
Attorney, Agent, or Firm—John H. Shurtleff

[57] ABSTRACT

Cyclic 6-membered to 8-membered 1,2-vinylenedioxy compounds of the general formula I

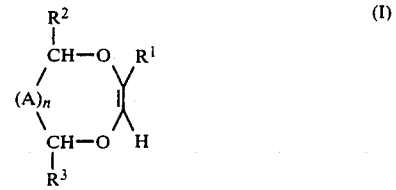

where A is

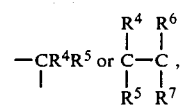

$R^1$ to $R^7$ independently of one another are each hydrogen, $C_1$–$C_8$-alkyl, $C_2$–$C_{16}$-alkoxyalkyl, $C_2$–$C_8$-alkenyl, $C_2$–$C_8$-alkynyl, $C_5$–$C_8$-cycloalkyl, aryl, $C_7$–$C_{10}$-alkylphenyl, $C_7$–$C_{10}$-phenalkyl, $C_8$–$C_{10}$-phenalkenyl or a heterocyclic structure, or $R^2$ and $R^3$, $R^2$ and $R^4$, $R^3$ and $R^4$, $R^2$ and $R^6$, $R^3$ and $R^6$, $R^4$ and $R^5$ or $R^6$ and $R^7$ together form a cycloaliphatic or heterocyclic ring, and $R^1$ to $R^7$ may furthermore carry substituents which are inert under the reaction conditions, and n is 0 or 1, are prepared by a process in which a cyclic 2-oxymethyl-1,3-dioxa compound or one of its derivatives of the general formula II

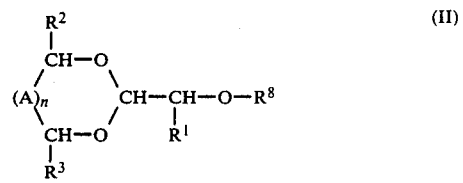

where $R^1$ to $R^7$, A and n have the abovementioned meanings, and $R^8$ is hydrogen or $C_1$–$C_{12}$-alkyl, is converted in the presence of an acidic catalyst at from 150° to 450° C. and under from 0.001 to 50 bar, some of the compounds obtained being novel.

8 Claims, No Drawings

PREPARATION OF CYCLIC 6-MEMBERED TO 8-MEMBERED VINYLENE-1,2-DIOXY COMPOUNDS

The present invention relates to a novel and improved process for the preparation of cyclic 6-membered to 8-membered vinylidene-1,2-dioxy compounds by thermal, acid-catalyzed ring enlargement of cyclic 2-oxymethyl-1,3-dioxa compounds or their derivatives.

J. Heterocycl. Chem. 17 (1980), 831–832 discloses that 1,4-dioxenes can be prepared from 2-alkoxy-1,4-dioxanes by acid-catalyzed elimination of alcohol.

Chem. Abstr. 103, 104,935r, J. Chem. Res. 273 (1977) and J. Org. Chem. 31 (2) (1966), 389–391, disclose certain 1,4-dioxep-2-ene compounds which carry a substituent at the double bond.

It is an object of the present invention to provide and improved process for obtaining cyclic 6-membered to 8-membered vinylene-1,2-dioxy compounds.

We have found that this object is achieved by a novel and improved process for the preparation of cyclic 6-membered to 8-membered vinylene-1,2-dioxy compounds, wherein a cyclic 2-oxymethyl-1,3-dioxa compound or one of its derivatives is converted in the presence of an acidic catalyst at from 150 to 450° C and under from 0.001 to 50 bar.

The cyclic 6-membered to 8-membered vinylene-1,2-dioxy compounds I are obtainable by the following method:

The reaction is carried out by bringing a cyclic 2-oxymethyl-1,3-dioxa compound or a derivative II into contact with an acidic catalyst, in accordance with the following equation:

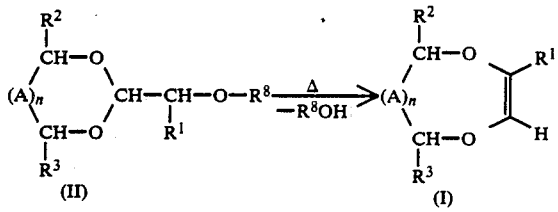

The reaction can be carried out both in the gas phase and, preferably, in the liquid phase, batchwise, preferably semicontinuously or particularly preferably continuously, at from 150° to 450° C. and under from 0.001 to 50 bar.

The gas phase reaction can be carried out, for example, at from 200° to 450° C. and under from 0.001 to 50 bar, preferably at from 250° to 350° C. and under from 0.02 to 25 bar, particularly preferably at from 270° to 350° C. and under from 0.05 to 10 bar.

In the reaction in the gas phase, a weight hourly space velocity (WHSV) of from 0.01 to 5, advantageously from 0.05 to 2, in particular from 0.1 to 2, g of starting material of the formula II per g of catalyst per hour is maintained. The gas phase reaction can be carried out in a fixed bed or in a fluidized bed.

Acidic solid heterogeneous catalysts are useful as catalysts for the novel process.

In particular, acidic zeolite catalysts are employed as catalysts for the process according to the invention. Zeolites which are suitable for this purpose are described in DE-A-35 13 75, DE-A-35 46 372, DE-A-36 30 684 and DE-A-36 38 010.

Catalysts which are suitable for the novel process are zeolites from the mordenite group or fine-pore zeolites of the erionite or chabazite type or zeolites of the faujasite type, for example Y, X or L zeolites. This group of zeolites also includes the ultrastable zeolites of the faujasite type, ie. dealuminated zeolites.

Particularly advantageous zeolites are those of the pentasil type. These zeolites may have different chemical compositions. They are aluminosilicate, borosilicate, ferrosilicate, beryllium silicate, gallium silicate, chromium silicate, arsenosilicate, antimony silicate and bismuth silicate zeolites or mixtures of these, as well as aluminogermanate, borogermanate, galliumgermanate and ferrogermanate silicates or mixtures of these. The aluminosilicate, borosilicate and ferrosilicate zeolites of the pentasil type are particularly suitable for the novel process.

The silicon-rich zeolites ($SiO_2/Al_2O_3 \geq 10$) which can be used include the ZSM types, ferrierite, NU-1 and Silicalit ® (a molecular sieve, ie. a silica polymorph).

The aluminosilicate, borosilicate and ferrosilicate zeolites thus prepared can be isolated and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay.

Advantageous catalysts are also obtained if the aluminosilicate or borosilicate zeolite isolated is molded directly after the drying process and is not calcined until after the molding procedure. The aluminosilicate and borosilicate zeolites prepared can be used in pure form, without a binder, as extrudates or pellets, the extrusion or peptizing assistants used being, for example, ethylcellulose, stearic acid, potato starch, formic acid, oxalic acid, acetic acid, nitric acid, ammonia, amines, silicoesters or graphite or mixtures of these.

If, because of its method of preparation, the zeolite is not in the catalytically active, acidic H form but, for example, in the Na form, this form can be converted completely or partially into the desired H form by ion exchange, for example with ammonium ions, and subsequent calcination or by treatment with acids.

If, when the zeolite catalysts are used according to the invention, deactivation due to coking occurs, it is advisable to regenerate the zeolites by a conventional method. By partial precoking, it is possible to adjust the activity of the catalyst to obtain optimum selectivity with respect to the desired reaction product.

In order to obtain very high selectivity, a high conversion and a long catalyst life, it may be advantageous to modify the zeolites. Modifications of this type are described in detail in DE-A-35 13 725, DE-A-35 46 372, DE-A-37 30 614 and DE-A-36 38 010.

In another possible method of modification, the molded or unmolded zeolite material is subjected to a treatment with acids, such as hydrochloric acid, hydrofluoric acid and phosphoric acid, and/or steam.

Further catalysts for the novel process are phosphates, in particular aluminum phosphates, silicon aluminum phosphates, silicon iron aluminum phosphates, cobalt aluminum phosphates, cerium phosphate, zirconium phosphates, boron phosphate, iron phosphate, strontium phosphates and mixtures of these.

Aluminum phosphate catalysts used for the novel process are, in particular, aluminum phosphates which have been synthesized under hydrothermal conditions and have a zeolite structure. The said aluminum phosphates are, for example, APO-5, APO-9, APO-11, APO-12, APO-14, APO-21, APO-25, APO-31 and APO-33. Syntheses of these compounds are described in EP-A-132 708, US-A-4 310 440 and US-A-4 473 663.

The silicon aluminum phosphates used for the novel process are, for example, SAPO-5, SAPO-11, SAPO-31 and SAPO-34. The synthesis of these compounds is described in, for example, EP-A-103 117 and US-A-3 440 871.

Modifying components, as described above for zeolites, can be applied to these phosphates by impregnation (immersion or spraying) or in some cases also by ion exchange. Modification with acids can also be carried out, as in the case of the zeolite catalysts.

Other examples of suitable acidic catalysts are the acidic oxides of elements of main groups III and IV and subgroups IV to VI of the Periodic Table, in particular oxides such as silica in the form of silica gel, kieselguhr or quartz, as well as titanium dioxide, zirconium dioxide, phosphorus oxides, vanadium oxides, niobium oxides, boron oxides, chromium oxides, molybdenum oxides, tungsten oxides or pumice or mixtures of these oxides. Furthermore, these oxides can be doped by applying modifying components, as described for the zeolite catalysts. The treatment with acids, as described above for the zeolite catalysts, is also a possible method of modification.

Catalysts impregnated with phosphoric acid or boric acid can also be used. Phosphoric acid or boric acid is applied to $SiO_2$, $Al_2O_3$, $TiO_2$ or pumice carriers, for example by impregnation or spraying.

Suitable catalysts are oxide catalysts, such as silica, silica catalysts which have been impregnated with phosphoric acid or sulfuric acid and calcined, and oxides, mixed oxides, phosphates or silicates of the elements boron, aluminum, titanium and zirconium, for example borosilicates, boron phosphates, aluminosilicates, aluminum phosphates and aluminum titanates. Those mixed oxides which have zeolite structures possess very advantageous properties. In some cases, silica is a sufficiently acidic catalyst.

The preferred liquid phase reaction can be carried out, for example, as a suspension, trickle-bed or liquid phase reaction at from 180° to 300° C. and under from 0.01 to 50 bar, preferably at from 200 to 280° C. and under from 0.02 to 25 bar, particularly preferably at from 220° to 260° C. and under from 0.02 to 15 bar. High-boiling liquids which are inert under the reaction conditions and have boiling points of from 150° to 500° C./1 bar, preferably from 180° to 450° C./1 bar, for example white oil, decalin, tetralin, diphenyl ether, silicone oils and in particular vacuum residues, are suitable liquid reaction media.

In a preferred embodiment, the starting material is pumped into the heated reaction medium, the acid required as a catalyst being either initially taken in the solvent or fed in together with the material to be reacted.

Suitable acidic catalysts are the catalysts stated for the gas phase reaction, as well as inorganic acids, such as sulfuric acid and phosphoric acid, or organic sulfonic acids, such as benzenesulfonic acid, p-toluenesulfonic acid and dodecylbenzenesulfonic acid.

It is also possible for a stream of gaseous hydrogen chloride, hydrogen bromide or sulfur trioxide to be passed into the reaction medium together with the starting material. It is also possible for metal compounds which act as Lewis acids, for example iron compounds, aluminum compounds, boron compounds, zinc compounds, titanium compounds, zirconium compounds or tin compounds, to be used as catalysts.

After the reaction, the products obtained are isolated from the reaction mixture by a conventional method. For example, the gaseous reaction products can be introduced immediately into a separation stage and separated into their individual components, for example in a fractionation column. Unconverted starting materials are, if desired, recycled to the reaction.

The compounds II can be prepared by a conventional method (Houben/Weyl, 4th Edition, Vol. 6/3, pages 203–293, 1965) from corresponding diols III and aldehydes IVa or their acetals IVb, in accordance with the equation below.

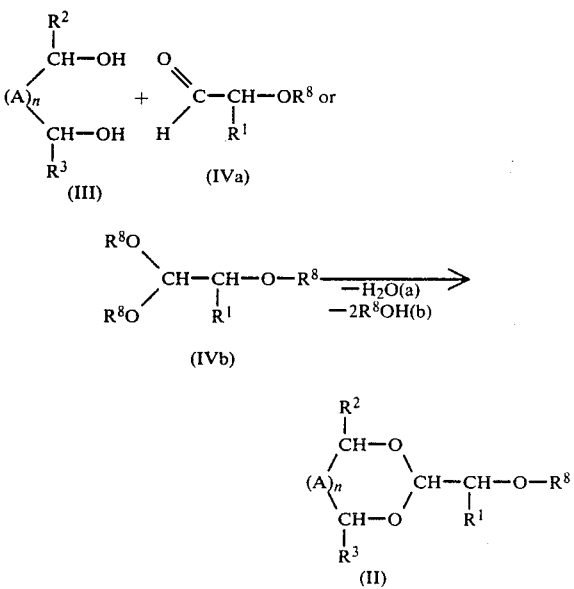

Some of the compounds III and IVa/b are known or can be prepared by a conventional method (for III: Houben/Weyl, 4th Edition, Vol. 6/1b, pages 1–638 (1984), and for IVa/b: Houben/Weyl, Vol. E3, pages 1–608 (1983)).

In particular, $R^1$ to $R^7$ in the formulae I to IV I.are, independently of one another, each hydrogen, straight-chain or branched $C_1$-$C_8$-alkyl, such as methyl, ethyl, propyl, isopropyl, n-butyl, isobutyl, sec-butyl, tert-butyl, pentyl, hexyl, heptyl or octyl, straight-chain or branched $C_2$-$C_{16}$-alkoxyalkyl, eg. methoxymethyl, ethoxymethyl, n-propoxymethyl, isopropoxymethyl, n-butoxymethyl, isobutoxymethyl, n-hexyloxymethyl, isohexyloxymethyl, n-heptyloxymethyl, isoheptyloxymethyl, methoxyethyl, ethoxyethyl, n-propoxyethyl, isopropoxyethyl, n-butoxyethyl, isobutoxyethyl, n-pentyloxyethyl, isopentyloxyethyl, n-hexyloxyethyl, isohexyloxyethyl, methoxypropyl, ethoxypropyl, n-propoxypropyl, isopropoxypropyl, n-butoxypropyl, isobutoxypropyl, n-pentyloxypropyl, isopentyloxypropyl, methoxybutyl, ethoxybutyl, n-propoxybutyl, isopropoxybutyl, n-butoxybutyl, isobutoxybutyl, methoxypentyl, ethoxypentyl, n-propoxypentyl, isopropoxypentyl, methoxyhexyl, ethoxyhexyl, methoxyheptyl, ethoxyheptyl, n-propoxyheptyl, isopropoxyheptyl, hexyloxyhepty, methoxyoctyl, ethoxyoctyl, n-butoxyoctyl, isobutoxyoctyl, hexyloxyoctyl or octyloxyoctyl, preferably $C_2$-$C_{10}$-alkoxyalkyl, particularly preferably $C_2$-$C_8$-alkoxyalkyl, straight-chain or branched $C_2$-$C_8$-alkenyl, such as vinyl, propenyl, isopropenyl, butenyl, isobutenyl, pentenyl, hexenyl, heptenyl or octenyl, straight-chain or branched $C_2$-$C_8$-alkynyl, such as ethynyl, propynyl, 3-methylbut-1-yn-1-yl, hexynyl or hexenynyl, $C_5$-$C_8$-cycloalkyl, such as cyclopentyl, cyclohexyl, cycloheptyl heptyl or cyclooctyl, aryl, such as phenyl or naphthyl, phenalkyl or alkylphenyl of 7 to 10 carbon atoms, such as tolyl, xylyl, phenethyl or benzyl, $C_8$-$C_{10}$-phenalkenyl, such as styryl and phenylbutenyl, or a heterocyclic structure, such as a heterocyclic or heteroaromatic radical, suitable heteroatoms being in particular oxygen, as well as nitrogen and sulfur. The heteroaromatic radicals advantageously have 5 or 6 ring members with 1 or 2 heteroatoms and may have a further fused 5-membered or 6-membered ring which is, for example, aromatic or heteroaromatic. The following radicals are examples: pyrrolyl, imidazolyl, pyrazolyl, triazolyl, tetrazolyl, oxazolyl, isoxazolyl, thiazolyl and thiadiazolyl.

Examples of heterocyclic radicals are heterocyclic radicals which are saturated or contain double bonds and have 1 or 2 heteroatoms, such as pyrrolidinyl, thiazolinyl, thiazolidinyl, piperidinyl, morpholinyl, dihydrofuranyl, tetrahydrofuranyl, dihydropyranyl, tetrahydropyranyl, dioxolanyl, dioxanyl, thioxanyl, tetrahydrothiophenyl, tetrahydrothiopyranyl and dithianyl.

Furthermore, the radicals $R^2$ and $R^3$, $R^2$ and $R^4$, $R^3$ and $R^4$, $R^2$ and $R^6$, $R^3$ and $R^6$, $R^4$ and $R^5$ or $R^6$ and $R^7$ together may form a further aliphatic or heteroaliphatic cyclic structure.

The bifunctional radical A is

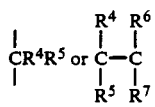

and n is 0 or 1.

$R^8$ in the compounds II and IVa and b is hydrogen or straight-chain or branched $C_1$-$C_{12}$-alkyl, such as methyl, ethyl, n-propyl, isopropyl, n-butyl, isobutyl, sec-butyl, tert-butyl, n-pentyl, isopentyl, sec-pentyl, tert-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, preferably straight-chain or branched $C_1$-$C_4$-alkyl, particularly preferably methyl, ethyl or n-butyl.

$R^1$ to $R^7$ may carry additional substituents, provided that these substituents are inert under the reaction conditions. These include, for example, the halogens fluorine, chlorine, bromine and iodine, nitro, cyano, thiol and thioether groups, sulfonyl and sulfoxyl, ester groups, such as methyl esters, ethyl esters or butyl esters, amide groups, such as unsubstituted amide or N-monosubstituted or N,N-disubstituted amide, such as N-methylamide, N-ethylamide, N-propylamide, N,N-dimethylamide, N,N-diethylamide or N-methyl-N-butylamide, and also cyclic or aromatic derivatives, such as morpholide or anilide, and in particular alkoxy, such as methoxy, ethoxy, n-propoxy, isopropoxy, n-butoxy or isobutoxy, and also further substituted radicals, eg. 2-methoxyethoxy or 2-chloroethoxy.

Novel compounds I are those in which A is $CR^4R^5$, n is 1 and $R^1$ is hydrogen, while novel compounds II are those in which A is $CR^4R^5$, n is 1 and $R^8$ is $C_1$-$C_{12}$-alkyl, and novel compounds III are those in which A is $CR^4R^5$, n is 1, $R^2$ and $R^3$ are each hydrogen, $R^4$ is $C_1$-$C_8$-alkoxyalkyl and $R^5$ is $C_2$-$C_8$-alkyl.

The cyclic 6-membered to 8-membered vinylene-1,2-dioxy compounds I are useful intermediates for the preparation of pharmacologically active compounds, active ingredients for crop protection and plastics.

EXAMPLES

EXAMPLE 1

A mixture of 380 g (5 moles) of 1,3-propanediol, 479 g (5.5 moles) of 85% strength methoxyacetaldehyde and 250 ml of cyclohexane was heated with 5 g of the ion exchanger Lewasorb ® AC 10 (Bayer Aktiengesellschaft) under a water separator until water no longer separated off. The ion exchanger was filtered off, the solvent was stripped off under reduced pressure and the residue was subjected to fractional distillation under reduced pressure. 587 g (89% yield) of 2-methoxymethyl-1,3-dioxane having a boiling range of 104° to 115° C./150 mbar were obtained.

250 g of vacuum gas oil and 2.5 g of dodecylbenzenesulfonic acid were initially taken at 250° C. in a stirred flask and nitrogen was passed in. 587 g of 2-methoxymethyl-1,3-dioxane were pumped in at a rate of 20 ml/h, and the reaction products were distilled off simultaneously. The crude distillate was then worked up by distillation and gave, in addition to methanol, 258 g of 1,4-dioxep-2-ene of boiling point 73°–80° C./200 mbar and 182 g of unconsumed starting material; this corresponded to a conversion with respect to 2-methoxymethyl-1,3-dioxane of 69% and a selectivity of 84%.

EXAMPLE 2

A mixture of 520 g (5 moles) of 2,2-dimethyl-1,3-propanediol, 479 g (5.5 moles) of 85% strength methoxy-acetaldehyde and 250 ml of cyclohexane was heated with 5 g of the ion exchanger Lewasorb AC 10 under a water separator until water no longer separated off. The ion exchanger was filtered off, the solvent was stripped off under reduced pressure and the residue was subjected to fractional distillation under reduced pressure. 632 g (79% yield) of 2-methoxymethyl-5,5-dimethyl-1,3-dioxane of boiling point 96° C./60 mbar were obtained.

250 g of vacuum gas oil were initially taken with 2.5 g of dodecylbenzenesulfonic acid at 250° C. in a stirred flask and nitrogen was passed in. 600 g of 2-methoxymethyl-5,5-dimethyl-1,3-dioxane were pumped in at a rate of 20 ml/h, and the reaction products were distilled off simultaneously. The crude distillate was then worked up by distillation and gave, in addition to methanol, 213 g of 6,6-dimethyl-1,4-dioxep-2-ene of boiling point 65°–67° C./100 mbar and 258 g of unconsumed starting material; this corresponded to a conversion with respect to 2-methoxymethyl-5,5-dimethyl-1,3-dioxane of 57% and a selectivity of 78%.

EXAMPLE 3

A mixture of 590 g (5 moles) of 2-ethyl-2-methyl1,3-propanediol, 479 g (5.5 moles) of 85% strength methoxyacetaldehyde and 500 ml of chloroform was heated with 10 g of pyridinium p-toluenesulfonate under a water separator until water no longer separated off. The remaining solution was deionized using a mixed-bed ion exchanger, the solvent was removed under reduced pressure and the residue was distilled. 774 g (89% yield)

of 2-methoxymethyl-5-ethyl-5-methyl-1,3-dioxane of boiling point 58° C./1 mbar were obtained.

250 g of vacuum gas oil were initially taken with 2.5 g of dodecylbenzenesulfonic acid at 250° C. in a stirred flask and nitrogen was passed in. 774 g of 2-methoxymethyl-5-ethyl-5-methyl-1,3-dioxane were pumped in at a rate of 20 ml/h, and the reaction products were distilled off simultaneously. The crude distillate was then worked up by distillation and gave, in addition to methanol, 297 g of 6-ethyl-6-methyl-1,4-dioxep-2-ene of boiling point 119°-121° C./400 mbar and 356 g of unconsumed starting material; this corresponded to a conversion with respect to 2-methoxymethyl-5-ethyl-5-methyl-1,3-dioxane of 54% and a selectivity of 71%.

EXAMPLE 4

A mixture of 670 g (5 moles) of 2-methoxymethyl2-methyl-1,3-propanediol, 479 g (5.5 moles) of 85% strength methoxyacetaldehyde and 250 ml of chloroform was heated with 10 g of pyridinium p-toluenesulfonate under a water separator until water no longer separated off. The solution was deionized using a mixed-bed ion exchanger, the solvent was stripped off under reduced pressure and the residue was subjected to fractional distillation under reduced pressure. 864 g (91% yield) of 2,5-dimethoxymethyl-5-methyl-1,3-dioxane of boiling point 95° C./10 mbar were obtained.

500 g of vacuum gas oil were initially taken with 5 g of dodecylbenzenesulfonic acid at 250° C. in a stirred flask and nitrogen was passed in. 150 g of 2,5-dimethoxymethyl-5-methyl-1,3-dioxane were pumped in at a rate of 30 ml/h, and the reaction products were distilled off simultaneously. The crude distillate was then worked up by distillation and gave, in addition to methanol, 23.3 g of 6-methoxymethyl-6-methyl-1,4-dioxep-2-ene of boiling point 101°-105° C./80 mbar and 85 g of unconsumed starting material; this corresponded to a conversion with respect to 2,5-dimethoxymethyl-5-methyl-1,3-dioxane of 43% and a selectivity of 43%.

EXAMPLE 5

352 g (4.4 moles) of 50% strength sodium hydroxide solution were added dropwise, in the course of 30 minutes, to a boiling mixture of 392 g (4 moles) of 2-isopropylacrolein, 1,280 g (40 moles) of methanol and 720 g (8.8 moles) of 30% strength formaldehyde and the refluxed mixture was then stirred for a further 60 minutes. It was then evaporated down, methyl isobutyl ketone was added and the residual water was separated off by azeotropic distillation. Precipitated sodium formate was filtered off and the filtrate was distilled. 504 g (78% yield) of 2-methoxymethyl-2-isopropyl-1,3-propanediol of boiling point 96°-100° C./1 mbar were obtained.

A mixture of 486 g (3 moles) of 2-methoxymethyl-2-isopropyl-1,3-propanediol, 287 g (3.3 moles) of 85% strength methoxyacetaldehyde and 250 ml of cyclohexane was heated with 5 g of the ion exchanger Lewasorb AC 10 under a water separator until water no longer separated off. The ion exchanger was filtered off, the solvent was stripped off under reduced pressure and the residue was subjected to fractional distillation under reduced pressure. 543 g (83% yield) of 2,5-dimethoxymethyl-5-isopropyl-1,3-dioxane of boiling point 95° C./1 mbar obtained.

250 g of vacuum gas oil were initially taken with 3.75 g of dodecylbenzenesulfonic acid at 230° C. in a stirred flask and nitrogen was passed in. 543 g of 2,5and dimethoxymethyl-5-isopropyl-1,3-dioxane were pumped in at a rate of 20 ml/h, and the reaction products were distilled off simultaneously. The crude distillate was then worked up by distillation and gave, in addition to methanol, 109 g of 6-methoxymethyl-6-isopropyl-1,4-dioxep-2-ene of boiling point 117°-118° C./45 of unconsumed starting material; this corresponded to a conversion with respect to 2,5-dimethoxymethyl-5-isopropyl-1,3-dioxane of 39% and a selectivity of 60%.

EXAMPLE 6

A mixture of 288 g (2 moles) of 1,1-dimethylolcyclohexane, 191 g (2.2 moles) of 85% strength methoxyacetaldehyde and 250 ml of cyclohexane was heated with 2 g of p-toluenesulfonic acid under a water separator until water no longer separated off. The resulting solution was washed with dilute sodium hydroxide solution, the solvent was stripped off under reduced pressure and the residue was subjected to fractional distillation under reduced pressure. 388 g (97% yield) of 3-methoxymethyl-2,4-dioxaspiro[5.5]undecane of boiling point 95° C./1 mbar were obtained.

250 g of vacuum gas oil were initially taken with 2.5 g of dodecylbenzenesulfonic acid at 250° C. in a stirred flask and nitrogen was passed in. 3-Methoxymethyl2,4-dioxaspiro[5.5]undecane was pumped in at a rate of 20 ml/h and the reaction products were distilled off simultaneously. The crude distillate was then worked up by distillation and gave, in addition to methanol, 83 g of 2,5-dioxaspiro[6.5]dodec-3-ene of boiling point 117° C./30 mbar and 268 g of unconsumed starting material; this corresponded to a conversion with respect to 3-methoxymethyl-2,4-dioxaspiro[5.5]undecane of 31% and a selectivity of 82%.

EXAMPLE 7

1 g of pyridinium p-toluenesulfonate was added to a mixture consisting of 152 g (2 moles) of 1,2-propanediol, 148 g (2 moles) of 85% strength methoxyacetaldehyde and 400 ml of cyclohexane, and the resulting mixture was refluxed under a water separator until water no longer separated off. The solution obtained was washed with water, the solvent was stripped off under reduced pressure and the residue was subjected to fractional distillation under reduced pressure. 245 g (93% yield) of 2-methoxymethyl-4-methyl-1,3-dioxolane of boiling point 79°-82° C./70 mbar were obtained.

(a) A total of 100 g of 2-methoxymethyl-4-methyl-1,3-dioxolane were passed, at 350° C., in the course of 5 hours, over 20 g of supported catalyst composed of 20% of phosphoric acid on silica. Methanol was first separated off from the condensate by means of cyclohexane, and the residue was then distilled. 21.2 g (28% yield) of 5-methyl-1,4-dioxene of boiling point 105° C./1013 mbar were obtained.

(b) 250 g of vacuum gas oil were initially taken with 2.5 g of dodecylbenzenesulfonic acid at 250° C. in a stirred apparatus. With simultaneous removal of the reaction products by distillation, a total of 176 g of 2-methoxymethyl-5-methyl-1,3-dioxolane were introduced in the course of nine hours together with a stream of nitrogen. Methanol was separated off from the distillate by means of cyclohexane and the residue was subjected to fractional distillation. 113 g (85% yield) of 5-methyl-1,4-dioxene of boiling point 105-106° C./1013 mbar were obtained.

EXAMPLE 8

2 g of pyridinium p-toluenesulfonate were added to a mixture consisting of 50 g (0.43 mole) of trans-1,2-cyclohexanediol, 54 g (0.47 mole) of 1,1,2-trimethoxyethane and 300 ml of cyclohexane, and the resulting mixture was refluxed under a water separator until methanol no longer separated off. The solution obtained was washed with water, the solvent was stripped off under reduced pressure and the residue was subjected to fractional distillation under reduced pressure. 64 g (86% yield) of 8-methoxymethyl-7,9-dioxabicyclo[4.3.0$^{1.6}$]nonane of boiling point 67°–70° C./1 mbar were obtained.

A total of 50 g of 8-methoxymethyl-7,9-dioxabicyclo[4.3.0$^{1.6}$]nonane were passed, at 300° C., in the course of 2.5 hours, over 40 g of silica extrudates, together with a stream of 40 l/h of $N_2$. Distillation of the condensate under reduced pressure gave 21 g (52% yield) of 2,5-dioxabicyclo[4.4.0]dec-3-ene of boiling point 40°–43° C./1 mbar.

The Examples which follow illustrate the invention where heterogeneous catalysts are used in the gas phase.

The catalysts used in Example 9° to 19 below are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (weight ratio of the mixture 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

Catalyst A is obtained by molding the borosilicate zeolite with a molding assistant to give 2 mm extrudates, which are dried at 110° C. for 16 hours and calcined at 500° C. for 24 hours.

Catalyst B

Catalyst B is prepared by doping catalyst A with $Ce(NO_3)_2$ and drying the product at 130° C. for 2 hours and calcining it at 540° C. for 2 hours. The Ce content is 1.8% by weight.

Catalyst C

Catalyst C is prepared similarly to catalyst B, except that impregnation is carried out using an aqueous solution of Pd nitrate and Ce nitrate instead of Ce nitrate. The Pd content is 1.3% by weight and the Ce content is 3.6% by weight.

Catalyst D

An aluminosilicate zeolite of the pentasil type was prepared under hydrothermal conditions, under autogenous pressure and at 150° C., from 65 g of finely divided $SiO_2$ and 20.3 g of $Al_2(SO_4)_3$ 18 $H_2O$ in 1 kg of aqueous 1,6-hexanediamine solution (weight ratio of the mixture 50:50) in a stirred autoclave. The crystalline reaction product was filtered off, washed thoroughly, dried at 110° C. for 24 hours and then calcined at 500° C. for 24 hours. This aluminosilicate zeolite contained 91.6% by weight of $SiO_2$ and 4.6% by weight of $Al_2O_3$.

The catalyst was molded with a molding assistant to give 2 mm extrudates, which were dried at 110° C. for 16 hours and calcined at 500° C. for 24 hours.

Catalyst E

Silicon aluminum phosphate-5 (SAPO-5) is prepared from a mixture of 200 g of 98% strength phosphoric acid, 136 g of boehmite, 60 g of silica gel (30% strength), 287 g of tripropylamine and 587 g of $H_2O$. This mixture is reacted at 150° C. in the course of 168 h under autogenous pressure. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

Catalyst F $BPO_4$ is prepared by combining 49 g of $H_3BO_3$ with 117 g of $H_3PO_4$. (75% strength) in a kneader, evaporating off excess water and molding the reaction product to give 3 mm extrudates. These extrudates are dried at 100° C. and calcined at 350° C. Catalyst F contains 8.77% by weight of B and 28.3% by weight of P.

Catalyst G

Catalyst G is a precipitated aluminum phosphate which is obtained by precipitation from $Al(NO_3)_3$/$H_3PO$. solution with $NH_3$ at a pH of 6–7. The precipitate is filtered off and then dried at 110° C. and calcined at 500° C. Catalyst G contains 28.5% by weight of Al and 13.2% by weight of P.

Catalyst H $CePO_4$ is obtained by precipitation from 52 g of $Ce(NO_3)_3$. 6 $H_2O$ and 56 g of $NaH_2PO_4$ . 2 $H_2O$. After filtration, the material is molded to give extrudates, which are dried at 120° C. and calcined at 450° C. Catalyst H contains 47.1% by weight of Ce and 12.7% by weight of P.

Catalyst I $SiO_2$, commercially available under the name D 11-10 ®.

Catalyst J $Al_2O_3$, commercially available under the name D 10-10 ®.

Catalyst K

D 10-10 ® is impregnated with $H_3BO_3$, dried at 110° C. and calcined at 500° C. for 5 hours. Catalyst K is composed of 85% of $Al_2O_3$ and 15% of $B_2O_3$.

EXAMPLES 9 TO 19

The reactions in the gas phase were carried out under isothermal conditions in a tubular reactor (coil, 0.6 cm internal diameter, 90 cm length) for not less than 6 hours. The reaction products were isolated by a conventional method and were characterized. Quantitative determination of the reaction products and of the starting materials was carried out by gas chromatography.

The exact reaction conditions and results are summarized in Table 1 below.

TABLE 1

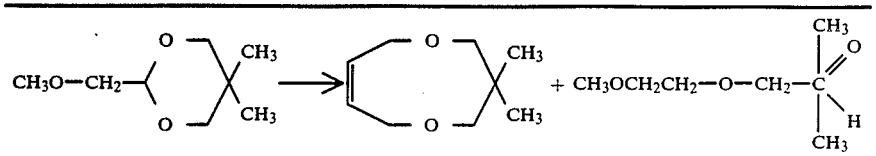

| Example | 9 | 10 | 11 | 12 | 13 | 14 | 15 | 16 | 17 | 18 | 19 |
|---|---|---|---|---|---|---|---|---|---|---|---|
| Catalyst | A | B | C | D | E | F | G | H | I | J | K |
| Temp., °C. | 300 | 350 | 350 | 300 | 350 | 350 | 350 | 350 | 350 | 350 | 350 |
| WHSV $h^{-1}$ | 2.9 | 3.0 | 3.0 | 3.0 | 2.3 | 3.3 | 2.3 | 2.3 | 3.0 | 3.0 | 3.0 |
| Conversion of educt, % | 61.3 | 95.4 | 95.5 | 75.2 | 100 | 36.4 | 78.2 | 33.3 | 66.3 | 25.8 | 43.8 |
| Selectivity for dioxepene, % | 53.0 | 61.7 | 61.3 | 49.1 | 41.0 | 95.1 | 38.4 | 71.2 | 43.2 | 37.2 | 35.0 |
| Selectivity for open-chain compound, % | 33.3 | 21.5 | 23.3 | 29.5 | 42.3 | 3.5 | 49.6 | — | 55.5 | 50.6 | 57.6 |

EXAMPLE 20

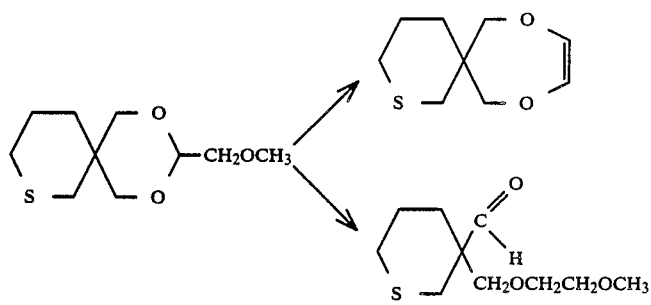

Over catalyst A, a conversion of 36% is achieved at 350° C. and using a space velocity of 2.4 g of a 50% strength solution of compound I in tetrahydrofuran per g of catalyst per hour. The selectivity with respect to the dioxepene derivative is 41% and that with respect to the aldehyde ether is 14%. At 300° C. under otherwise identical reaction conditions, the conversion is 8.2% and the selectivity 58% for the dioxepene derivative.

EXAMPLE 21

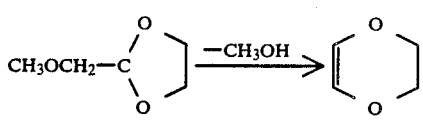

Methoxyacetaldehyde glycol acetate (dissolved in tetrahydrofuran in a ratio of 50:50) undergoes complete conversion over a boron phosphate catalyst at 350° C. and a WHSV of 3 $h^{-1}$, the selectivity with respect to dehydroxioxane being 58%.

EXAMPLE 22

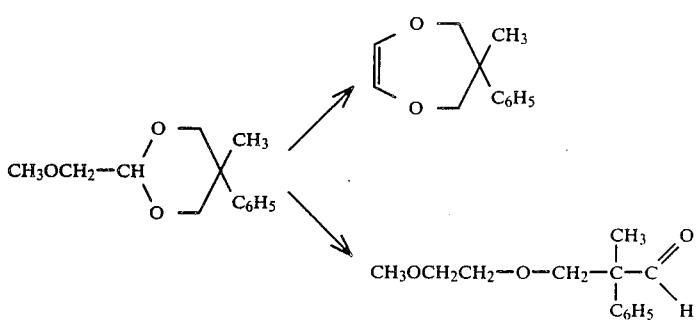

Methoxyacetaldehyde-2-methyl-2-phenyl-propanediol acetal undergoes 20% conversion at 300° C. and a WHSV of 3 $h^{-1}$. The selectivity with respect to the dioxepene derivative is 56.5%.

Over catalyst D under identical reaction conditions, 30% conversion and 26.5% selectivity are found for the dioxepene derivative or 20.3% for the open-chain compound.

We claim:

1. A process for the preparation of a cyclic 6-membered to 8-membered vinylene-1,2-dioxy compound of the formula I

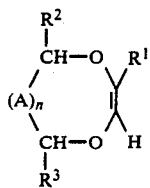
(I)

where A is

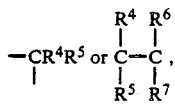

$R^1$ to $R^7$ independently of one another are each hydrogen or an aliphatic, cycloaliphatic, aromatic, aliphatic-aromatic or heterocyclic radical, or $R^2$ and $R^3$, $R^2$ and $R^4$, $R^3$ and $R^4$, $R^2$ and $R^6$, $R^3$ and $R^5$, $R^4$ and $R^6$ or $R^6$ and $R^7$ together form a cycloaliphatic or heterocyclic ring, and $R^1$ to $R^7$ may furthermore carry substituents which are inert under the reaction conditions, and n is 0 or 1, wherein a cyclic 2-oxymethyl-1,3-dioxa compound or one of its derivatives of the formula II

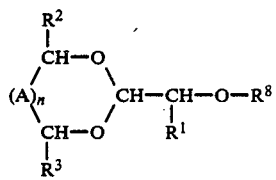
(II)

where $R^1$ to $R^7$, A and n have the abovementioned meanings, and $R^8$ is hydrogen or $C_1$-$C_{12}$-alkyl, is converted in the presence of an acidic catalyst at from 150° to 450° C. and under from 0.001 to 50 bar.

2. A process as claimed in claim 1, wherein a starting compound of the formula II where $R^1$ to $R^7$ independently of one another are each hydrogen, $C_2$-$C_8$-alkyl, $C_2$-$C_6$-alkoxyalkyl, $C_2$-$C_8$-alkenyl, $C_2$-$C_8$-alkynyl, $C_5$-$C_8$-cycloalkyl, aryl, $C_7$-$C_{10}$-alkylphenyl, $C_7$-$C_{10}$-phenalkyl, $C_8$-$C_{10}$-phenalkyl or a heterocyclic structure is used.

3. A process as claimed in claim 1, wherein the reaction to convert the compound II into the compound I is carried out in the liquid phase and in the presence of an organic sulfonic acid.

4. A process as claimed in claim 1, wherein the reaction to convert the compound II into the compound I is carried out in the gas phase and in the presence of an acidic fixed bed catalyst.

5. A process as claimed in claim 1, wherein the reaction to convert the compound II into the compound I is carried out in the liquid phase and in the presence of dodecylbenzenesulfonic acid.

6. A process as claimed in claim 1, wherein the reaction to convert the compound II into the compound I is carried out in the gas phase and in the presence of a zeolite of the pentasil type.

7. A process as claimed in claim 1, wherein the reaction to convert the compound II into the compound I is carried out in the liquid phase at from 180° to 300° C. and under from 0.01 to 50 bar.

8. A process as claimed in claim 1, wherein the reaction to convert the compound II into the compound I is carried out in the gas phase at from 200° to 450° C. and under from 0.001 to 50 bar.

* * * * *

UNITED STATES PATENT AND TRADEMARK OFFICE
CERTIFICATE OF CORRECTION

PATENT NO. : 5,003,089
DATED : March 26, 1991
INVENTOR(S) : Franz Merger, Juergen Frank, Wolfgang Hoelderich, Toni Dockner and Manfred Sauerwald It is certified that error appears in the above-identified patent and that said Letters Patent is hereby corrected as shown below:

In Claim 1, column 13, line 21: change "$R^5$" (only occurrence) to --$R^6$--;

change "$R^6$" (second occurrence) to --$R^5$--.

In Claim 2, column 14, line 7: change "$C_2$" to --$C_1$--;

line 8: change "$C_6$" to --$C_{16}$--.

Signed and Sealed this

Twenty-eighth Day of July, 1992

Attest:

DOUGLAS B. COMER

Attesting Officer

Acting Commissioner of Patents and Trademarks